United States Patent
Takeuchi et al.

(10) Patent No.: US 9,062,030 B2
(45) Date of Patent: Jun. 23, 2015

(54) PYRAZOLE AZETIDINE DERIVATIVES AS SPHINGOSINE 1-PHOSPHATE (S1P) RECEPTOR MODULATORS

(71) Applicant: Allergan, Inc., Irvine, CA (US)

(72) Inventors: Janet A. Takeuchi, Anaheim, CA (US); Ling Li, Irvine, CA (US); Wha Bin Im, Irvine, CA (US); Ken Chow, Newport Coast, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/187,557

(22) Filed: Feb. 24, 2014

(65) Prior Publication Data

US 2014/0243307 A1 Aug. 28, 2014

Related U.S. Application Data

(60) Provisional application No. 61/768,962, filed on Feb. 25, 2013.

(51) Int. Cl.
*C07D 231/54* (2006.01)
*A61K 31/00* (2006.01)
*C07D 403/10* (2006.01)

(52) U.S. Cl.
CPC .................................. *C07D 403/10* (2013.01)

(58) Field of Classification Search
None
See application file for complete search history.

(56) References Cited

FOREIGN PATENT DOCUMENTS

WO 2005123677 A1 12/2005

OTHER PUBLICATIONS

Cross, L.C. et al, Rules for the Nomenclature of Organic Chemistry, Section E: Stereochemistry, Pure & Appl. Chem., 1976, 11-30, 45.
Heinrich Stahl, Pharmaceutical Salts, Handbook of Pharmaceutical Salts, 2002, 329-345, International Union of Pure and Applied Chemistry, Verlag Helvetica Chemica Acta-Zürich.
Zecri, Frederic J. et al, Pyrazole derived from (+I-3-carene: a novel potent. selective scaffold for sphingosine-1-phosphate (S1 P1 I receptor agonists, Bioorganic & Medicinal Chemistry Letters (2010),20(1),35-37.
International Search Report, PCT/US2014/017967, May 15, 2014.
Bolli, Martin et al, Novel S1P1 Receptor Agonists—Part 1: From Pyrazoles to Thiophenes, Journal of Medicinal Chemistry, Dec. 12, 2013, 9737-9755, 56(23).
Bolli, Martin et al, Novel S1P1 Receptor Agonists—Part 2: From Bicyclo[3.1.0]hexane-Fused Thiophenes to Isobutyl Substituted Thiophenes, Journal of Medicinal Chemistry, Dec. 17, 2013, 78-97, 57(1).
Kurata, Haruto et al, Structure-Activity Relationship Studies of S1P Agonists With a Dihydronaphthalene Scaffold, Bioorganic & Medicinal Chemistry Letters, 2012, 144-148, 22.

*Primary Examiner* — Nyeemah A Grazier
(74) *Attorney, Agent, or Firm* — Barbara C. Potts

(57) ABSTRACT

The present invention relates to pyrazole azetidine derivatives, processes for preparing them, pharmaceutical compositions containing them and their use as pharmaceuticals as modulators of sphingosine-1-phosphate receptors.

6 Claims, No Drawings

PYRAZOLE AZETIDINE DERIVATIVES AS SPHINGOSINE 1-PHOSPHATE (S1P) RECEPTOR MODULATORS

RELATED APPLICATIONS

This application claims the benefit of U.S. Provisional Patent Application Ser. No. 61/768,962 filed Feb. 25, 2013, the disclosure of which is hereby incorporated in its entirety herein by reference.

FIELD OF THE INVENTION

The present invention relates to pyrazole azetidine derivatives, processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1-phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

A group of novel pyrazole derivatives which are potent and selective sphingosine-1-phosphate modulators has been discovered. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation.

In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

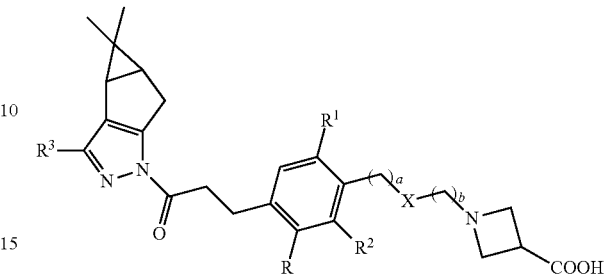

Formula I wherein:
R is H, optionally substituted $C_{1-6}$ alkyl, —$OC_{1-3}$ alkyl, halogen, optionally substituted $C_{6-10}$ aryl, optionally substituted heterocycle, CN, $NO_2$, $C(O)R^4$, $NR^5R^6$ or OH;
$R^1$ is H, halogen, optionally substituted $C_{1-6}$ alkyl, optionally substituted $C_{6-10}$ aryl, optionally substituted heterocycle;
$R^2$ is H, halogen, optionally substituted $C_{1-6}$ alkyl, optionally substituted $C_{6-10}$ aryl, optionally substituted heterocycle;
$R^3$ is H, optionally substituted $C_{1-6}$ alkyl;
$R^4$ is H, OH or optionally substituted $C_{1-6}$ alkyl;
a is 0, 1, 2 or 3;
b is 0, 1, 2 or 3;
X is S, O, $NR^5$ or $CHR^6$;
$R^5$ is H, optionally substituted $C_{1-6}$ alkyl; and
$R^6$ is H, optionally substituted $C_{1-6}$ alkyl.

In another aspect the invention provides a compound of Formula I, wherein:
R is H, optionally substituted $C_{1-6}$ alkyl or halogen;
$R^1$ is H, halogen or optionally substituted $C_{1-6}$ alkyl;
$R^2$ is H, halogen or optionally substituted $C_{1-6}$ alkyl;
$R^3$ is H or optionally substituted $C_{1-3}$ alkyl;
a is 0 or 1;
b is 0 or 1;
X is $CHR^6$; and
$R^6$ is H.

In another aspect the invention provides a compound of Formula I, wherein:
R is H or optionally substituted $C_{1-6}$ alkyl;
$R^1$ is H or optionally substituted $C_{1-6}$ alkyl;
$R^2$ is H or optionally substituted $C_{1-6}$ alkyl;
$R^3$ is methyl or ethyl;
a is 0 or 1;
b is 0 or 1;
X is $CHR^6$; and
$R^6$ is H.

In another aspect the invention provides a compound of Formula I, wherein:
R is H;
$R^1$ is H;
$R^2$ is H;
$R^3$ is methyl;
a is 0;
b is 0;
X is $CHR^6$; and
$R^6$ is H.

The term "alkyl", as used herein, refers to saturated, monovalent or divalent hydrocarbon moieties having linear or branched moieties or combinations thereof and containing 1 to 6 carbon atoms. One methylene (—$CH_2$—) group, of the alkyl can be replaced by oxygen, sulfur, sulfoxide, nitrogen, carbonyl, carboxyl, sulfonyl, or by a divalent $C_{3-6}$ cycloalkyl. Alkyl groups can be substituted by halogen, hydroxyl, cycloalkyl, amino, non-aromatic heterocycles, carboxylic acid, phosphonic acid groups, sulphonic acid groups, phosphoric acid.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by $C_{1-3}$ alkyl groups or halogens.

The term "halogen", as used herein, refers to an atom of chlorine, bromine, fluorine, iodine.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. Heterocycle can be monocyclic or polycyclic. The heterocyclic ring can be interrupted by a C=O; the S heteroatom can be oxidized. Heterocycles can be monocyclic or polycyclic. Heterocyclic ring moieties can be substituted by hydroxyl, $C_{1-3}$ alkyl or halogens.

The term "aryl" as used herein, refers to an organic moiety derived from an aromatic hydrocarbon consisting of a ring containing 6 to 10 carbon atoms by removal of one hydrogen. Aryl can be monocyclic or polycyclic. Aryl can be substituted by halogen atoms, —O$C_{1-3}$ alkyl, $C_{1-3}$ alkyl, CN, —C(O)H or —C(O)($C_{1-3}$ alkyl), NH($C_{1-3}$ alkyl), $NH_2$, N($C_{1-3}$ alkyl)($C_{1-3}$ alkyl), $NO_2$ or hydroxyl. Usually aryl is phenyl. Preferred substitution site on aryl are meta and para positions.

The term "hydroxyl" as used herein, represents a group of formula "—OH".

The term "carbonyl" as used herein, represents a group of formula "—C(O)".

The term "carboxyl" as used herein, represents a group of formula "—C(O)O—".

The term "sulfonyl" as used herein, represents a group of formula "—$SO_2$".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—P(O)(OH)$_2$".

The term "phosphoric acid" as used herein, represents a group of formula "—(O)P(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.
1-(4-{3-oxo-3-[3,4,4-Trimethyl-3b,4,4a,5-tetrahydro-1H-cyclopropa[3,4]cyclopenta[1,2-c]pyrazol-1-yl] propyl}benzyl)azetidine-3-carboxylic acid is a compound of the invention.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahl & Camille G. Wermuth (Eds), Verlag Helvetica Chimica Acta-Zurich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by 51 P modulation: not limited to the treatment of diabetic retinopathy, other retinal degenerative conditions, dry eye, angiogenesis and wounds.

Therapeutic utilities of S1P modulators are Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immunosuppression: rheumatoid arthritis, Crohn's disease, Graves' disease, inflammatory bowel disease, multiple sclerosis, Myasthenia gravis, Psoriasis, ulcerative colitis, autoimmune uveitis, renal ischemia/perfusion injury, contact hypersensitivity, atopic dermatitis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries; Organ transplants: renal, corneal, cardiac and adipose tissue transplants.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereoisomers thereof.

The present invention concerns the use of a compound of Formula I or a pharmaceutically acceptable salt thereof, for the manufacture of a medicament for the treatment of Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immunosuppression: rheumatoid arthritis, Crohn's disease, Graves' disease, inflammatory bowel disease, multiple sclerosis, Myasthenia gravis, Psoriasis, ulcerative colitis, autoimmune uveitis, renal ischemia/perfusion injury, contact hypersensitivity, atopic dermatitis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual nontoxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene. Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001 to about 5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for drop wise application are usually made of suitable inert, non-toxic plastic material, and generally contain between about 0.5 and about 15 ml solution. One package may contain one or more unit doses. Especially preservative-free solutions are often formulated in non-resalable containers containing up to about ten, preferably up to about five units doses, where a typical unit dose is from one to about 8 drops, preferably one to about 3 drops. The volume of one drop usually is about 20-35 μl.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic schemes set forth below, illustrate how compounds according to the invention can be made.

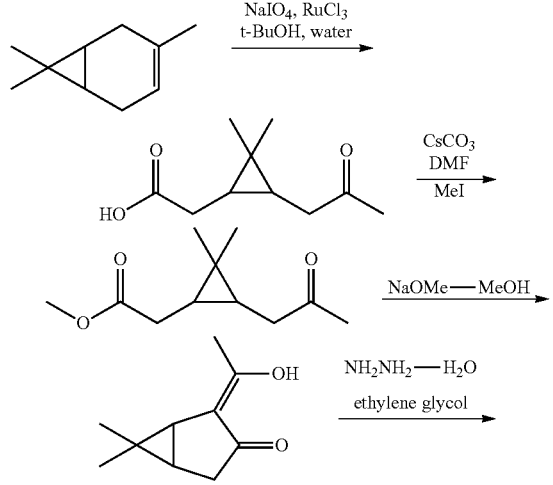

Scheme 1

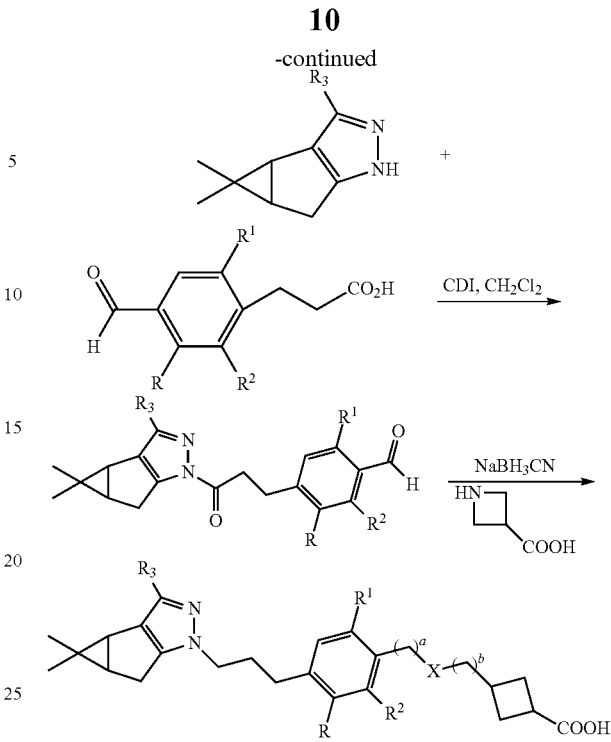

The following abbreviations are used in Scheme 1 and in the examples:
NaIO$_4$ sodium periodate
RuCl$_3$×H$_2$O ruthenium(II) chloride hydrate
EtOAc ethylacetate
NaCl sodium chloride
NaOH sodium hydroxide
MgSO$_4$ magnesium sulfate
DMF dimethylformamide
CsCO$_3$ cesium carbonate
MeI methyl iodide
NaOMe sodium methoxide
MeOH methanol
Et$_2$O diethylether
NaHCO$_3$ sodium bicarbonate
CDCl$_3$ deuterated chloroform
CH$_2$Cl$_2$ dichloromethane
MPLC medium pressure liquid chromatography
CD$_3$OD deuterated methanol
NH$_2$NH$_2$—H$_2$O hydrazine monohydrate
CDI 1,1'-carbonyldiimidazole
NaBH$_3$CN sodium cyanoborohydride Those skilled in the art will be able to routinely modify and/or adapt the following scheme to synthesize any compounds of the invention covered by Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereoisomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACDLabs version 12.5; and intermediates and reagent names used in the examples were generated with software such as Chem Bio Draw Ultra version 12.0 or Auto Nom 2000 from MDL ISIS Draw 2.5 SP1.

In general, characterization of the compounds is performed according to the following methods. Proton nuclear magnetic resonance ($^1$H NMR) and carbon nuclear magnetic resonance ($^{13}$C NMR) spectra were recorded on a Varian 60 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, coupling constant(s) J in hertz (Hz), integrated intensity).

EXAMPLE 1

Intermediate 1

2-(2,2-dimethyl-3-(2-oxopropyl)cyclopropyl)acetic acid

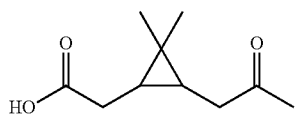

A 3-neck, 2 L flask equipped with a mechanical stirrer, condenser with Argon, thermometer, and temperature controlled heating mantle was charged with t-butanol (157 mL), water (315 mL) and 3-carene (25 g, 0.184 mol). To the stirred resultant cloudy suspension was added NaIO$_4$ (140 g, 0.654 mol) and RuCl$_3$×H$_2$O (0.63 g, 0.003 mol). The vigorously stirred thick mixture was heated at 35-45° C. for 2 hr, then at 45-50° C. for 1 hr and another 30 min at 55° C. The thick mixture was cooled to 30° C. and filtered. The solid was pressed with dental dam and rinsed with diethyl ether (200 mL). The original aqueous filtrate was extracted with 2:1 EtOAc:Hexanes (250 mL). The organic layer and ether filtrate were combined and washed with 20% aqueous NaCl (85 mL), then extracted with a solution of 10 g of NaOH in 620 mL of water. The aqueous layer was cooled in an ice bath and acidified to pH 1 with 12 N HCl (28 mL) and extracted with diethyl ether (3×225 mL). The ether layers were combined and washed with brine (110 mL). The organic layer was dried over anhydrous MgSO$_4$ (30 g) overnight. The organic layer was filtered and concentrated to give 20 g of Intermediate 1 as a brown oil (59%).

$^1$H NMR (60 MHz, CDCl$_3$): δ 11.4 (s, 1H), 2.2 (s, 3H), 2.5-2.1 (m, 4H), 1.1 (s, 3H), 0.95 (s, 3H), 1.3-0.9 (m, 2H) ppm.

EXAMPLE 2

Intermediate 2

Methyl 2-(2,2-dimethyl-3-(2-oxopropyl)cyclopropyl)acetate

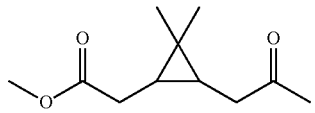

A 3-neck, 500 mL flask equipped with a stir bar, condenser, oil bath, and Ar inlet, was charged with Intermediate 1, (19.0 g, 0.10 mol), DMF (100 mL), and CsCO$_3$ (18.6 g, 0.057 mol). To the resultant mixture after stirring 10 min was added MeI (6.86 mL, 0.11 mol). The mixture was heated at 40° C. for 1 hr. The reaction mixture was cooled with an ice bath. The solids were filtered. The filtrate was quenched with 18% (w/w) aqueous NaCl (500 mL). The organic layer was separated and the aqueous layer was extracted with 1:1 Et$_2$O: Hexanes (2×200 mL). The combined organic layers were washed with water (200 mL) and dried over anhydrous MgSO$_4$ (20 g) overnight. The organic layer was filtered and concentrated to give 15.6 g of Intermediate 2, as an orange oil (79%).

$^1$H NMR (60 MHz, CDCl$_3$): δ 3.6 (s, 3H), 2.4--2.3 (m, 4H), 2.2 (s, 3H), 1.1 (s, 3H), 0.95 (s, 3H), 1.2-0.9 (m, 2H) ppm.

EXAMPLE 3

Intermediate 3

(Z)-2-(1-hydroxyethylidene)-6,6-dimethylbicyclo [3.1.0]hexan-3-one

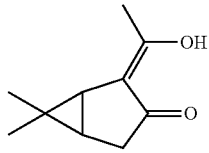

A 3-neck, 250 mL flask equipped with a stir bar, condenser, oil bath, and Ar inlet, was charged with Intermediate 2, (15 g, 0.0757 mol) in methanol (47 mL). To this solution was added 25% NaOMe in MeOH (28 mL, 0.129 mol). The solution changed from orange to red. The reaction was heated 15 min and refluxed for 25 min. The mixture was cooled and extracted with toluene (2×25 mL). The aqueous layer was cooled in an ice bath and 20% Aq HCl (25 mL) was added dropwise with stirring to pH 2. The aqueous layer was then extracted with Et$_2$O (2×100 mL). The ether layers were combined and washed with 5% aqueous NaHCO$_3$ (2×25 mL) filtered through phase separation paper and concentrated to give 9.0 g of Intermediate 3, as a light orange oil (71%).

$^1$H NMR (60 MHz, CDCl$_3$): δ 2.6-2.3 (m, 2H), 2.0 (s, 3H), 1.9-1.6 (m, 1H), 1.4-1.3 (m, 1H), 1.05 (s, 3H), 0.9 (s, 3H) ppm.

EXAMPLE 4

Intermediate 4

3,4,4-trimethyl-3b,4,4a,5-tetrahydro-1H-cyclopropa [3,4]cyclopenta [1,2-c]pyrazole

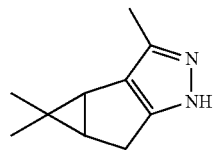

A 3-neck, 250 mL flask equipped with a stir bar, condenser, and Ar inlet, was charged with Intermediate 3, (9.0 g, 0.054 mol) in methanol (45 mL) and glacial acetic acid (9 mL) resulting in an orange solution. To this solution all at once was added hydrazine hydrate (3.15 g, 0.063 mol). The solution was warm to the touch. After stirring for 2 hr at room temperature no starting material was present by HPLC. The reaction was cooled in an ice bath and 1M 50% NaOH was added dropwise to pH 9-10. A solid formed and was left stirring for 20 min, filtered, and dried to give 7.6 g of Intermediate 4, as an orange solid (87%).

$^1$H NMR (60 MHz, CDCl$_3$): δ 3.0-2.4 (m, 2H), 2.2 (s, 3H), 1.8-1.6 (m, 2H), 1.0 (s, 3H), 0.6 (s, 3H) ppm.

EXAMPLE 5

Intermediate 5

4-(3-oxo-3-(3,4,4-trimethyl-3b,4,4a,5-tetrahydro-1H-cyclopropa[3,4]cyclopenta[1,2-c]pyrazol-1-yl) propyl)benzaldehyde

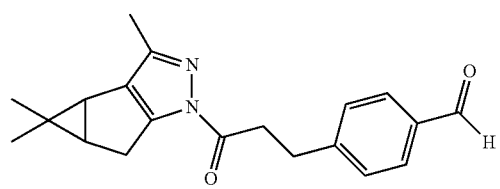 [SMILES: Cc1nn(C(=O)CCc2ccc(C=O)cc2)c2c1C1C(C2)C1(C)C]

A 3-neck, 250 mL flask equipped with a stir-bar, and Ar inlet, was charged with 3-(4-formylphenyl)propionic acid (1.64 g, 0.0092 mol) in CH$_2$Cl$_2$ (40 mL). To this suspension was added all at once carbonyl diimidazole (1.57 g, 0.0097 mol). The resulting colorless solution was stirred for 40 min until outgassing stopped. The Intermediate 4, (1.50 g, 0.0092 mol) was added to the solution. After 1.25 hr the reaction was complete by HPLC. The reaction was diluted with CH$_2$Cl$_2$ (40 mL) and washed with 1M HCl (40 mL), H$_2$(40 mL), and saturated aqueous NaHCO$_3$ (40 mL). The organic layer was filtered through phase separation paper and concentrated to 2.67 g of an orange oil (95% by HPLC). This oil was purified by MPLC 0-70% EtOAc in Hexanes. Fractions with 32-42% EtOAc in Hexanes contained product and were concentrated to give 2.25 g of Intermediate 5, as a viscous yellow oil (76%).

$^1$H NMR (300 MHz, CDCl$_3$): δ 10.0 (s, 1H), 7.82 (d, 2H), 7.42 (d, 2H), 3.40 (m, 2H), 3.20-3.0 (m, 3H), 2.90-2.80 (d, 1 H), 2.21 (s, 3H), 1.80 (m, 2H), 1.05 (s, 3H), 0.68 (s, 3H) ppm.

EXAMPLE 6

Compound 1

1-{4-[3-oxo-3-(3,4,4-trimethyl-3b,4,4a,5-tetrahydro-1H-cyclopropa [3,4]cyclopenta[1,2-c]pyrazol-1-yl) propyl]benzyl}azetidine-3-carboxylic acid

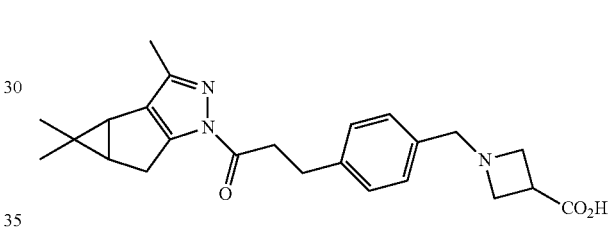

To a solution of Intermediate 5, (86 mg, 0.27 mmol) in methanol (10 mL) was added 3-azetidinecarboxylic acid ([CAS 36476-78-5] 28 mg, 0.28 mmol). After the reaction mixture was stirred at RT for 2.5h, sodium cyanoborohydride (17 mg, 0.27 mmol) was added. After the mixture was stirred at RT for 1.5h, the mixture was concentrated and purified by MPLC (100% methanol in ethyl acetate) to give 53 mg of Compound 1, as a colorless solid.

$^1$H NMR (600 MHz, CD$_3$OD) δ 7.10-7.45 (m, 4H), 4.02 (s, 2H), 3.75-3.96 (m, 4H), 3.21-3.33 (m, 3H), 2.96-3.06 (m, 2H), 2.88-2.95 (m, 1H), 2.76-2.83 (m, 1H), 2.16 (s, 3H), 1.76-1.84 (m, 2H), 1.08 (s, 3H), 0.64 (s, 3H).

Biological Data

Compounds were synthesized and tested for S1P1 activity using the GTP γ$^{35}$S binding assay. These compounds may be assessed for their ability to activate or block activation of the human S1P1 receptor in cells stably expressing the S1P1 receptor.

GTP γ$^{35}$S binding was measured in the medium containing (mM) HEPES 25, pH 7.4, MgCl$_2$ 10, NaCl 100, dithiothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH 7.4, $MgCl_2$ 10 and NaCl 100). Filters were dried and mixed with scintillant, and counted for $^{35}S$ activity using a β-counter. Agonist-induced GTP $\gamma^{35}S$ binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Table 1 shows activity potency: S1P1 receptor from GTP $\gamma^{35}S$: nM, ($EC_{50}$).

TABLE 1

| IUPAC name | S1P1 $EC_{50}$ (nM) |
|---|---|
| 1-{4-[3-oxo-3-(3,4,4-trimethyl-3b,4,4a,5-tetrahydro-1H-cyclopropa [3,4]cyclopenta[1,2-c]pyrazol-1-yl)propyl]benzyl}azetidine-3-carboxylic acid | 450 |

What is claimed is:

1. A compound represented by Formula I, its enantiomers, diastereoisomers, tautomers or a pharmaceutically acceptable salt thereof,

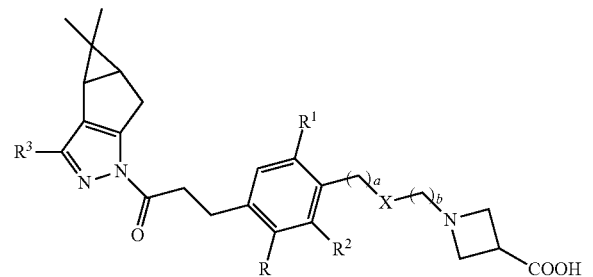

Formula I wherein:
R is H, optionally substituted $C_{1-6}$ alkyl, —$OC_{1-3}$ alkyl, halogen, optionally substituted $C_{6-10}$ aryl, optionally substituted heterocycle, CN, $NO_2$, $C(O)R^4$, $NR^5R^6$ or OH;
$R^1$ is H, halogen, optionally substituted $C_{1-6}$ alkyl, optionally substituted $C_{6-10}$ aryl, or optionally substituted heterocycle;
$R^2$ is H, halogen, optionally substituted $C_{1-6}$ alkyl, optionally substituted $C_{6-10}$ aryl, or optionally substituted heterocycle;
$R^3$ is H or optionally substituted $C_{1-6}$ alkyl;
$R^4$ is H, OH or optionally substituted $C_{1-6}$ alkyl;
a is 0, 1, 2 or 3;
b is 0, 1, 2 or 3;
X is S, O, $NR^5$ or $CHR^6$;
$R^5$ is H or optionally substituted $C_{1-6}$ alkyl; and
$R^6$ is H or optionally substituted $C_{1-6}$ alkyl.

2. The compound according to claim 1, wherein:
R is H, optionally substituted $C_{1-6}$ alkyl or halogen;
$R^1$ is H, halogen or optionally substituted $C_{1-6}$ alkyl;
$R^2$ is H, halogen or optionally substituted $C_{1-6}$ alkyl;
$R^3$ is H or optionally substituted $C_{1-3}$ alkyl;
a is 0 or 1;
b is 0 or 1;
X is $CHR^6$; and
$R^6$ is H.

3. The compound according to claim 1, wherein:
R is H or optionally substituted $C_{1-6}$ alkyl;
$R^1$ is H or optionally substituted $C_{1-6}$ alkyl;
$R^2$ is H or optionally substituted $C_{1-6}$ alkyl;
$R^3$ is methyl or ethyl;
a is 0 or 1;
b is 0 or 1;
X is $CHR^6$; and
$R^6$ is H.

4. The compound according to claim 1, wherein:
R is H;
$R^1$ is H;
$R^2$ is H;
$R^3$ is methyl;
a is 0;
b is 0;
X is $CHR^6$; and
$R^6$ is H.

5. The compound according to claim 1 which is:
1-{4-[3-oxo-3-(3,4,4-trimethyl-3b,4,4a,5-tetrahydro-1H-cyclopropa[3,4]cyclopenta[1,2-c]pyrazol-1-yl)propyl]benzyl]azetidine-3-carboxylic acid.

6. A pharmaceutical composition comprising as an active ingredient a therapeutically effective amount of a compound according to claim 1, and a pharmaceutically acceptable adjuvant, diluent or carrier.

* * * * *